US005876350A

United States Patent [19]
Lo et al.

[11] Patent Number: 5,876,350
[45] Date of Patent: Mar. 2, 1999

[54] EKG BASED HEART RATE MONITOR WITH DIGITAL FILTER AND ENHANCEMENT SIGNAL PROCESSOR

[75] Inventors: Thomas Ying-Ching Lo, Fremont, Calif.; Yuh Show Tsai, Nashville, Tenn.

[73] Assignee: Salutron, Inc., Fremont, Calif.

[21] Appl. No.: 745,928

[22] Filed: Nov. 7, 1996

Related U.S. Application Data

[63] Continuation-in-part of Ser. No. 554,373, Nov. 8, 1995, Pat. No. 5,738,104, issued Apr. 14, 1998.

[51] Int. Cl.$^6$ .............................. A61B 5/024; A61B 5/02
[52] U.S. Cl. ......................... 600/519; 600/502; 600/503
[58] Field of Search ................................... 128/689, 690, 128/706; 600/502, 503, 519

[56] References Cited

U.S. PATENT DOCUMENTS

| | | |
|---|---|---|
| D. 302,194 | 7/1989 | Charnitski . |
| 3,212,496 | 10/1965 | Preston . |
| 3,218,638 | 11/1965 | Honig . |
| 3,648,688 | 3/1972 | O'Hanlon et al. . |
| 3,688,776 | 9/1972 | Kenny . |
| 3,702,113 | 11/1972 | Blockley . |
| 3,704,706 | 12/1972 | Herczfeld et al. . |

(List continued on next page.)

FOREIGN PATENT DOCUMENTS

| | | |
|---|---|---|
| 248 8893 | 4/1990 | Japan . |
| 212 6829 | 5/1990 | Japan . |
| 308 6148 | 4/1991 | Japan . |
| 507 6501 | 3/1993 | Japan . |
| 061 1701 | 2/1994 | Japan . |
| 507 6500 | 3/1996 | Japan . |
| 2 165 352 | 4/1986 | United Kingdom . |

OTHER PUBLICATIONS

T.Y. Lo & P.C. Tang, "A fast Band–Pass Filter for ECG Processing," Proceedings–Fourth Annual Conference, IEEE Engineering in Medicine and Biology Society, pp. 321–325, Sep. 1982.

Hamilton, P.S. and Tompkins, W.J., "Quantitative Investigation of QRS Detection Rules Using the MIT/BIH Arrythmia Database" *IEEE Transactions on Biomedical Engineering* 33(12) :1157–1165 (Dec. 1986).

Lo, T.Y. and Tang, P.C., "A Fast Band–Pass Filter for ECG Processing" *IEEE Frontiers of Engineering in Health Care—1982*, pp. 321–325 (1982).

Sun, Y. et al., "Microcontroller–Based Real–Time QRS Detection" *Biomed. Instrumentation & Technology*, pp. 477–484 (Nov./Dec. 1992).

Suppappola, S. and Sun, Y., "Nonlinear Transforms of ECG Signals for Digital QRS Detection: A Quantitative Analysis" *IEEE Transactions on Biomedical Engineering* 41 (4) :397–400 (Apr. 1994).

Suzuki, Y., "Self–Organizing QRS–Wave Recognition in ECG Using Neural Networks" *IEEE Transactions on Neural Networks* 6(6) :1469–1477 (Nov. 1995).

*Primary Examiner*—William E. Kamm
*Assistant Examiner*—Carl H. Layno
*Attorney, Agent, or Firm*—Townsend and Townsend and Crew LLP

[57] ABSTRACT

A convenient low-cost heart rate monitor. In one embodiment, a digital filter structure includes a low pass filter having a notch at 60 Hz and a bandpass filter which amplifies signals in a frequency range from 10–40 Hz and has a notch at 60 Hz. This digital filter has a recursive structure and uses integer coefficients to simplify and speed up the calculations. A four bit microcontroller may implement the digital filter. The output of the digital filter is subject to enhancement signal processing to emphasize QRS complexes indicative of human heartbeats.

21 Claims, 8 Drawing Sheets

U.S. PATENT DOCUMENTS

| | | |
|---|---|---|
| 3,767,195 | 10/1973 | Dimick . |
| 3,769,974 | 11/1973 | Smart et al. . |
| 3,796,213 | 3/1974 | Stephens . |
| 3,807,388 | 4/1974 | Orr et al. . |
| 3,923,041 | 12/1975 | Stasz et al. . |
| 3,949,388 | 4/1976 | Fuller . |
| 3,978,848 | 9/1976 | Yen et al. . |
| 3,993,047 | 11/1976 | Peek . |
| 4,038,976 | 8/1977 | Hardy et al. . |
| 4,052,979 | 10/1977 | Scherr et al. . |
| 4,054,779 | 10/1977 | Wilke . |
| 4,063,551 | 12/1977 | Sweeney . |
| 4,083,366 | 4/1978 | Gombrich et al. . |
| 4,096,854 | 6/1978 | Perica et al. . |
| 4,105,020 | 8/1978 | Matsuoka et al. . |
| 4,120,294 | 10/1978 | Wolfe . |
| 4,129,124 | 12/1978 | Thalmann . |
| 4,163,447 | 8/1979 | Orr . |
| 4,166,454 | 9/1979 | Meijer . |
| 4,185,621 | 1/1980 | Morrow . |
| 4,195,642 | 4/1980 | Price et al. . |
| 4,221,223 | 9/1980 | Linden . |
| 4,223,683 | 9/1980 | Lown et al. .............................. 128/706 |
| 4,224,948 | 9/1980 | Cramer et al. . |
| 4,230,127 | 10/1980 | Larson . |
| 4,248,244 | 2/1981 | Charnitski et al. ...................... 128/706 |
| 4,256,117 | 3/1981 | Perica et al. . |
| 4,280,506 | 7/1981 | Zurcher . |
| 4,295,472 | 10/1981 | Adams . |
| 4,301,808 | 11/1981 | Taus . |
| 4,305,401 | 12/1981 | Reissmueller et al. . |
| 4,307,728 | 12/1981 | Walton . |
| 4,319,581 | 3/1982 | Cutter . |
| 4,331,154 | 5/1982 | Broadwater et al. . |
| 4,353,152 | 10/1982 | O'Connor et al. . |
| 4,358,105 | 11/1982 | Sweeney, Jr. . |
| 4,406,290 | 9/1983 | Walbeoffe-Wilson et al. . |
| 4,407,295 | 10/1983 | Steuer et al. . |
| 4,409,983 | 10/1983 | Albert . |
| 4,412,546 | 11/1983 | Barthels . |
| 4,420,000 | 12/1983 | Bailey . |
| 4,425,921 | 1/1984 | Fujisaki et al. . |
| 4,450,001 | 5/1984 | Ewing . |
| 4,464,123 | 8/1984 | Glover et al. . |
| 4,478,224 | 10/1984 | Bailey ..................................... 128/706 |
| 4,478,225 | 10/1984 | Ewing . |
| 4,517,986 | 5/1985 | Bilgutay . |
| 4,572,207 | 2/1986 | Yoshimi et al. . |
| 4,573,478 | 3/1986 | Arnold et al. . |
| 4,625,733 | 12/1986 | Säynäjäkangas . |
| 4,641,658 | 2/1987 | Lepper . |
| 4,667,682 | 5/1987 | Ihlenfeld, III . |
| 4,753,243 | 6/1988 | Mawhinney et al. . |
| 4,819,860 | 4/1989 | Hargrove et al. . |
| 4,834,532 | 5/1989 | Yount . |
| 4,860,759 | 8/1989 | Kahn et al. . |
| 4,883,055 | 11/1989 | Merrick . |
| 4,905,704 | 3/1990 | Walloch . |
| 4,909,259 | 3/1990 | Tehrani . |
| 4,938,228 | 7/1990 | Righter et al. . |
| 5,003,983 | 4/1991 | Dingwell et al. . |
| 5,094,244 | 3/1992 | Callahan et al. . |
| 5,100,374 | 3/1992 | Kagayama . |
| 5,156,147 | 10/1992 | Warren et al. . |
| 5,215,097 | 6/1993 | Watabe . |
| 5,228,449 | 7/1993 | Christ et al |
| 5,243,992 | 9/1993 | Eckerie et al. . |
| 5,243,993 | 9/1993 | Alexander et al. . |
| 5,262,414 | 11/1993 | Aung et al. . |
| 5,297,557 | 3/1994 | Reichl . |
| 5,314,389 | 5/1994 | Dotan . |
| 5,318,487 | 6/1994 | Golen et al. . |
| 5,323,784 | 6/1994 | Shu . |
| 5,337,753 | 8/1994 | Lekhtman . |
| 5,365,934 | 11/1994 | Leon et al. . |
| 5,394,879 | 3/1995 | Gorman . |
| 5,400,794 | 3/1995 | Gorman . |
| 5,406,952 | 4/1995 | Barnes et al. . |
| 5,417,716 | 5/1995 | Franberg et al. . |
| 5,431,170 | 7/1995 | Mathews . |
| 5,503,160 | 4/1996 | Pering et al. ........................... 128/706 |
| 5,628,326 | 5/1997 | Arand et al. . . . |

EKG BASED HEART RATE MONITOR WITH DIGITAL FILTER AND ENHANCEMENT SIGNAL PROCESSOR

STATEMENT OF RELATED APPLICATIONS

This application is a continuation-in-part and claims priority from U.S patent application Ser. No. 08/554,373, filed Nov. 8, 1995, now U.S Pat. No. 5,738,104, issued Apr. 14, 1998.

BACKGROUND OF THE INVENTION

The present invention pertains to the field of pulse monitors, and, more particularly, to the field of pulse monitors that use EKG signals to detect the pulse rate.

In the prior art, two basic types of pulse rate monitors exist. The first type uses visible or infrared radiation which is projected through the skin to detect from radiation reflected from or penetrated through capillaries under the skin, pulsations of blood flow. Typically, these devices come in the form of a digital watch with a photodetector on the face of the watch or as a desktop unit or unit that clips to a belt with a clip connected to base unit, the clip for attaching to a fingertip or earlobe. Visible or infrared light passing through the skin is detected by the photodetector and gives an indication of pulsations in blood flow in capillaries. From these pulsations, the pulse rate is calculated.

Numerous examples of this type pulse monitor exist as they are commonly found on fitness equipment such as treadmills, stationary bicycles and stair climbing machines. Another example of this type system is a pulse rate monitor wrist watch made by Casio. This watch reads both blood pressure and pulse. The watch has two sensors on top of the watch. The sensor on the lower left of the face of the watch is a photosensor which is to be covered with the wearer's right index finger. The other sensor is to be covered by the right middle finger and is an electrode to pick up the EKG signals. The bottom plate of the watch body serves as the other electrode.

There are several disadvantages to the photosensor/flow pulsation detectors. First, the finger position on the photosensor must be stable. Also, the force pressing the finger or ear lobe to the photodetector must be nominal. If the force is too high, the blood flow will be cut off, and no detection of blood flow pulsations can occur. If the force is too low, then any slight motion between the body and the sensor may cause inaccurate readings. Also, the reliability of the readings depends upon the ambient illumination (unless a separate photodiode supplies light for transmission through the skin) and upon the wavelength. Further, the flow pulse in a capillary looks like a sinusoidal waveform in shape. This makes it difficult to distinguish legitimate flow pulse signals from sinusoidally shaped noise waveforms.

The second type of pulse rate monitor is the EKG type. These type pulse monitors work by picking up an EKG signal from the heart muscle itself and calculating the pulse rate from the EKG signal. One example of this type system is a pulse rate monitor wrist watch made by Casio. This watch reads both blood pressure and pulse. The watch has two sensors on top of the watch. The sensor on the lower left of the face of the watch is a photosensor which is to be covered with the wearer's right index finger and which detects fluctuations in light passing through the finger from ambient sources to determine when blood flow pulses occur. The sensor on the lower right of the face is one of two sensors for an EKG signal. The bottom surface of the watch is the other sensor for picking up the EKG signal. To use this watch to read blood pressure and pulse, the user must first use another independent instrument to measure blood pressure and pulse in an at-rest condition. These readings are then input to the watch. After inputting this data, the watch takes about 10–20 heartbeats with the user's fingers in contact with the two contacts on the face of the watch. During these 10–20 heartbeats, the watch learns the timing between the EKG signals picked up by the EKG contacts and the corresponding blood flow pulses in an at-rest condition. This timing serves as a reference for determination of blood pressure. The operative principle is determination by the watch of the timing between the EKG signal that causes the left ventricle to pump blood to the resulting pulse of blood flow detected by the photodetector in the capillaries of the wearer's fingertip.

A drawback of this design is that the timing between the EKG pulse and the blood flow pulse changes with fitness level as the aerobic effect takes over and new blood flow paths are formed in the body. As a result, the manufacturer recommends that the basic at-rest data read from an independent instrument be updated every three months. This is inconvenient unless the owner of the watch also owns independent instruments to measure blood pressure and pulse rate. Further, the watch is incapable of measuring only pulse rate without also measuring blood pressure.

EMG noise is particularly troublesome in EKG pulse monitors because its frequency is in the same range as the frequency of the sought after EKG signal. Therefore, special signal processing must be accomplished to separate EMG noise from the desired EKG signal. One type of signal processing methodology that has been tried in the prior art is autocorrelation. The EKG signal is sensed by probes which are typically mounted on the handles of exercise equipment which the user grabs while exercising. The signals sensed by these probes, which contain the EKG signal, are passed through an autocorrelator which performs a correlation calculation between a piece of the signal represented by one buffer's worth of digital samples and an adjacent portion of the signal in time represented by another set of samples. Signal indication logic monitors the output of the autocorrelator for the presence of a periodic signal and generates a synthetic candidate heart rate signal that has the same frequency as the periodic signal in the output of the autocorrelator. The difficulty with this approach is that the EMG signals during exercise are also periodic and will cause peaks in the autocorrelator output that do not represent periodic EKG signal.

The class of products described above are generally used by health conscious people while working out. Because of the drawbacks of the approaches described above, there has arisen a need for a reliable pulse monitor that is small and can be worn on the wrist or attached to exercise equipment and requires no electrode gel or moisture or chest strap and which can accurately find the EKG signal despite low signal to noise ratio.

SUMMARY OF THE INVENTION

A convenient low-cost heart rate monitor is provided by virtue of the present invention. In one embodiment, a digital filter structure includes a low pass filter having a notch at 60 Hz and a bandpass filter which amplifies signals in a frequency range from 10–40 Hz and has a notch at 60 Hz. This digital filter has a recursive structure and uses integer coefficients to simplify and speed up the calculations. A four bit microcontroller may implement the digital filter. The output of the digital filter is subject to enhancement signal processing to emphasize QRS complexes indicative of human heartbeats.

In accordance with a first aspect of the present invention, a heart rate monitor includes at least two electrical contacts for detecting the electrical signals when placed in contact with the body, an analog circuit that conditions the electrical signals, an analog-to-digital converter coupled to receive an analog output signal from the analog circuit and convert the analog signals to a plurality of digital samples, a digital filter for receiving the digital samples and suppressing noise signals that have frequencies below about 5–15 Hertz, and signals having frequencies above about 25–40 Hertz to generate filtered data, the digital filter being a recursive filter having integer coefficients, and an enhancement signal processor to receive the filtered data and highlight signals therein that have predetermined characteristics of QRS complexes in human heartbeat signals so as to generate enhanced digital data.

In accordance with a second aspect of the present invention, a method for distinguishing pulses caused by heartbeats from other pulses includes steps of discarding pulses that arrive at times inconsistent with plausible beat-to-beat variation in heartbeat rate as representing artifacts rather than heartbeats, and discarding pulses having amplitudes varying more than a predetermined amount from previously received pulses representing heartbeats.

A further understanding of the nature and advantages of the inventions herein may be realized by reference to the remaining portions of the specification and the attached drawings.

DESCRIPTION OF SPECIFIC EMBODIMENTS

Figure 1:
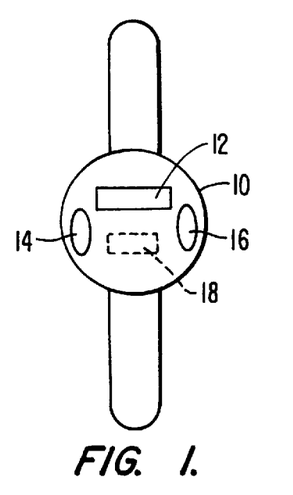
FIG. 1 shows a typical application in a digital wrist watch for the EKG type heart rate monitor according to the teachings of the invention.

Referring to FIG. 1, there is shown a typical application in a digital wrist watch for the EKG type heart rate monitor according to the teachings of the invention. The digital watch 10 includes a display such as LCD display 12 which is used to display the time, and when the pulse monitor mode is selected, displays the user's heart rate. In some embodiments, a separate display can be used to show the pulse rate with the time simultaneously displayed in display 12. The digital watch embodiment uses a three contact approach to help eliminate noise. Two electrical contacts 14 and 16 are placed on the front of the watch for the user to place his or her fingers on when the pulse mode is entered. A third electrical contact is located on the back side of the watch and is indicated in phantom at 18. The three contacts are connected to a differential amplifier inside the watch so that common mode noise is suppressed. It should be understood that the present invention is not limited to three contacts. The circuitry and software described below is incorporated into the watch 10 so that the unit is stand alone.

Figure 2:
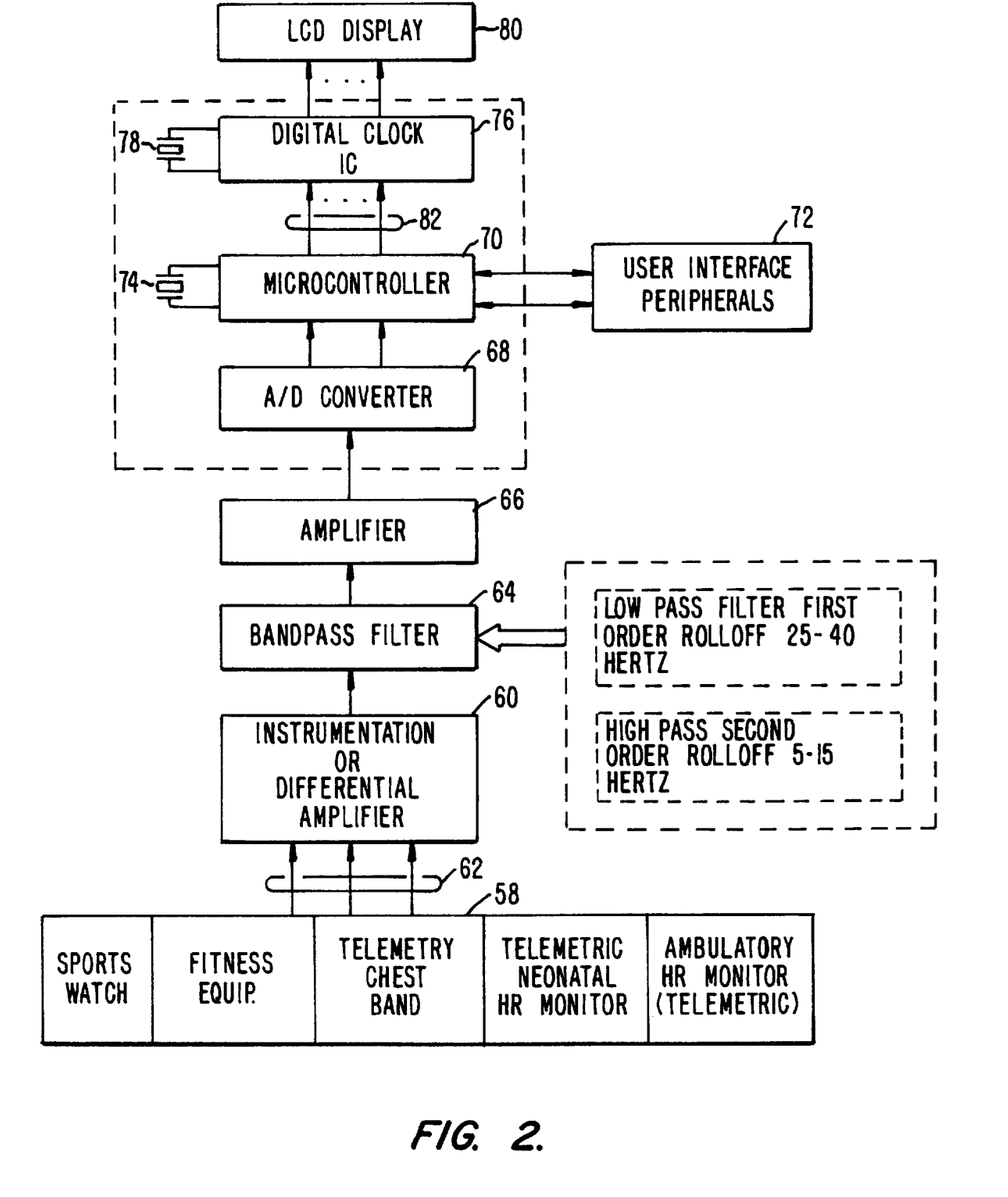
FIG. 2 is a block diagram of the preferred embodiment of the electronics of the invention.

Referring to FIG. 2, there is shown a block diagram of the preferred embodiment for circuitry to implement the teachings of the invention. Block 58 represents the electrical contacts of any of the embodiments discussed above. Block 60 is a differential amplifier or instrumentation amplifier that is coupled via bus 62 to the contacts. The differential amplifier amplifies the analog signals on the three conductors of bus 62. The common input on bus 62 is coupled to analog ground and the two remaining conductors are coupled to the plus and minus inputs of the differential amplifier. The differential amplifier serves to provide gain and to simultaneously eliminate common mode noise in the signal such 60/50 Hertz hum etc. The gain of the differential amplifier is set at a relatively low figure of 1–10 to prevent saturation of the operational amplifiers therein by the low frequencies that are still in the analog signal.

Next, the output of the amplifier is filtered by an active analog bandpass filter 64. Active filters using RC components in operational amplifier circuits are used to implement the bandpass filter. The passband of this filter is centered on some frequency between 5 and 20 Hertz, preferably 10–15 Hertz, and has a passband of approximately 5–40 Hertz. The purpose of this bandpass filter is to remove high frequencies from the analog signal to prevent aliasing. The low frequency corner of the passband also eliminates DC components and any low frequency drift of the baseline caused by respiration muscle contractions or other muscle contractions such as typically occur when the user is exercising. The gain of the bandpass filter is set between 1 and 10 at the center frequency. A passive bandpass filter could be used, but generally is not preferred since it requires too many components and the rolloff is not sharp enough. In the preferred embodiment, the passband filter is comprised of two separate hardware filters: a low pass filter with a first order rolloff and a corner frequency between 25–40 Hertz; and a high pass filter with a second order rolloff with a corner frequency of from 5–15 Hertz. The reason these two filters have different order rolloffs is to allow the differentiator to emphasize the high frequency components in the signal in a manner described below. In other words, the steeper rolloff on the low frequency corner provides better selectivity, while the less steep rolloff on the high frequency corner allows more high frequency component to reach the differentiator such that the differentiator will generate bigger slope numbers because of the sharp peaks in the signal represented by the data reaching the differentiator because of the higher content of high frequency components in the analog signals reaching the analog-to-digital converter. These sharper corners cause the differentiation operation in the digital signal processing portions of the circuit to be described below to generate higher peaks. These higher peaks are filtered out by the moving average function, but in the process, the average rises thereby causing the EKG signals to stand out better against the background noise.

Next, the analog signal is amplified in amplifier 66 which has a gain of 50–1000 so that the overall gain is about 1000–10,000.

Next, the analog output of the amplifier 66 is applied to the input of an analog-to-digital converter (hereafter AD converter) 68, which, in the preferred embodiment is integrated onto the microcontroller integrated circuit. The analog signal is converted to 8-bit digital samples at a sampling rate of 180 Hertz, or some other multiple of 60 Hertz preferably. Other sampling rates can also be used so long as the high frequency components of the real signal from the electrodes have been filtered out prior to the real signal reaching the analog-to-digital converter. If these high frequency components have not been filtered out, alias signals will appear in the EKG frequency range resulting from beating of the sampling rate with the high frequency components. This is why use of an analog bandpass filter in front of the analog-to-digital converter is preferred. Different numbers of bits in each sample could be used as well as a higher or lower sampling rate, but 180 Hertz is preferred to make the digital filtering easier since the 180 Hertz sampling rate is a multiple of the 60 Hertz frequency of a common source of noise. Further, the coefficients for the digital signal processing stages described below are set for a sample rate of 180 samples per second, so if other sample rates are used, the coefficients must be optimized again. In some embodiments, the AD converter is part of a microcontroller integrated circuit 70. The AD converter should be able to operate on a 3 volt supply or some supply voltage easily achievable with batteries and, for size considerations in some embodiments, preferably has a serial format output data stream if the AD converter is not integrated onboard the microcontroller.

The digital data stream from the AD converter is input to the microcontroller 70 for further signal processing to be described below. The microcontroller is preferably a 4-bit or 8-bit machine such as a Samsung KS57C2408 or Hitachi H8/3812 or equivalent. These microcontrollers have on-board analog-to-digital converter, dual clocks, LCD drive and buzzer drives. There is no need for an on-board DSP or a separate DSP since the digital filter coefficients are integers which substantially simplifies and speeds up processing in the software filtering modules. The microcontroller is also coupled to a number of user interface peripherals represented by block 72. The user interface peripherals include LCD displays, mode control switches, buzzer(s), sensors for monitoring track/wheel speed or as part of an automatic feedback loop which will cause more drag on the wheel/track when the heart rate drops below a target range, and output ports to which different resistors may be connected to change the gain of the operational amplifiers, output signals to implement automatic load variation in embodiments where the drag on the belt/wheel is automatically varied in accordance with the user's heart rate, such as circuitry to change the gears on a mountain bike to a lower gear or higher gear automatically based upon the user's heart rate, and alarm units to give users audible alarms when something is not working or needs adjustment. The microcontroller incorporates a main clock 74 which can be shut down in power down mode while an independent digital clock also incorporated within the microcontroller is not disabled during power down mode.

In some embodiments, a separate digital clock integrated circuit 76 with its own clock 78 serves to keep track of the time/date etc. and control the display thereof. In alternative embodiments, the digital clock chip can be any digital clock chip where display 80 displays only time and date so long as the clock chip has an interface to the microcontroller 70 to receive heart rate data. However, in the preferred embodiment, digital clock IC 76 is incorporated into the microcontroller and receives for display data encoding the heart rate reading, calories burned, speed, distance covered, exercise time etc. via the conductors of bus 82 for display on LCD display 80.

Figure 3A:
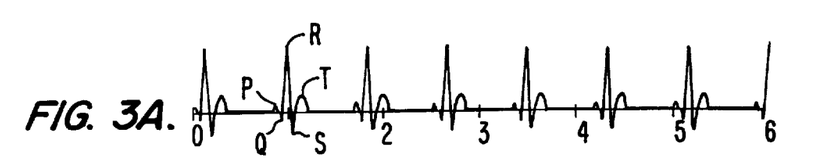
FIGS. 3A–3G are illustrations of some of the waveforms involved in illustrating some of the issues dealt with by the teachings of the invention.

There follows a discussion of the digital signal processing implemented by the firmware which controls operations of the microcontroller 70. However, to better understand the approach used, the characteristics of a typical EKG signal and an EKG signal with noise will first be discussed. Referring to FIGS. 3A–3G show a number of waveforms FIG. 3A shows a typical EKG signal, which is sometimes referred to as a QRS complex. An EKG signal is comprised of a first small positive peak designated as P in FIG. 3A, followed by a negative peak designated Q. After the negative Q peak, a very large positive peak immediately follows which is designated as R in FIG. 3A. The R peak is immediately followed by a negative S peak which is immediately followed by a smaller positive T peak. The slope of the R peak is symmetrical on both sides and has a unique characteristic value.

Figure 3B:
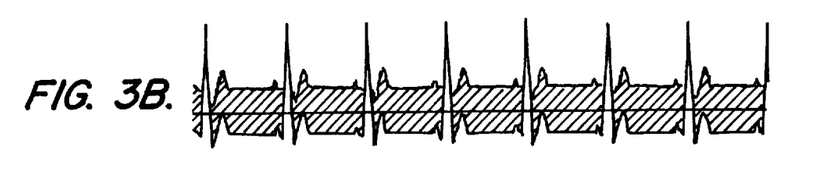
Figure 3C:
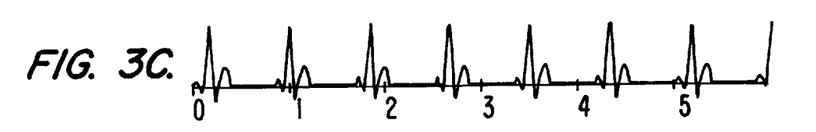
Figure 3D:
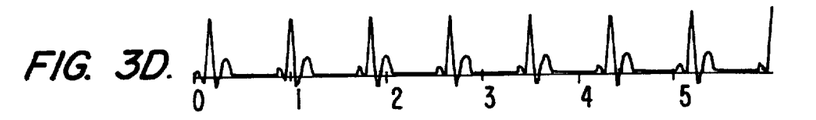
Figure 3E:
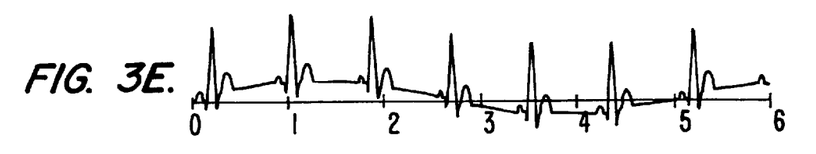
Figure 3F:
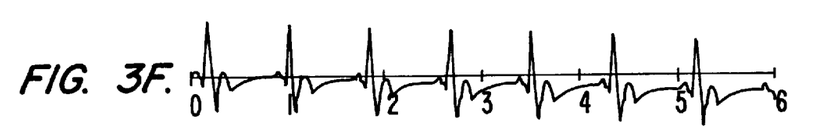
Figure 3G:
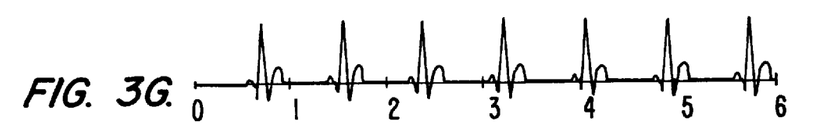

FIG. 3B shows a EKG signal superimposed with 60 Hertz line interference. FIG. 3C shows the result of passing the signal of FIG. 3B through a second order Butterworth lowpass filter. The signal of FIG. 3C still exhibits some 60 Hertz noise. FIG. 3E shows an EKG signal superimposed upon a low frequency noise sources such as respiration EMG or exercise EMG signals. FIG. 3F shows the result of passing the signal of FIG. 3B through a second order Butterworth high pass filter showing distortion of the signal from the action of the filter. FIG. 3D shows the signal resulting from passing the noisy signal of FIG. 3B through an integer coefficient low pass filter such as is used in the invention. FIG. 3G shows the signal resulting from passing the signal of FIG. 3E through an integer coefficient high pass filter such as is used in the invention. Both low and high pass integer coefficient filters are used in the invention to eliminate both 60 Hertz noise and low frequency noise.

Figure 4:
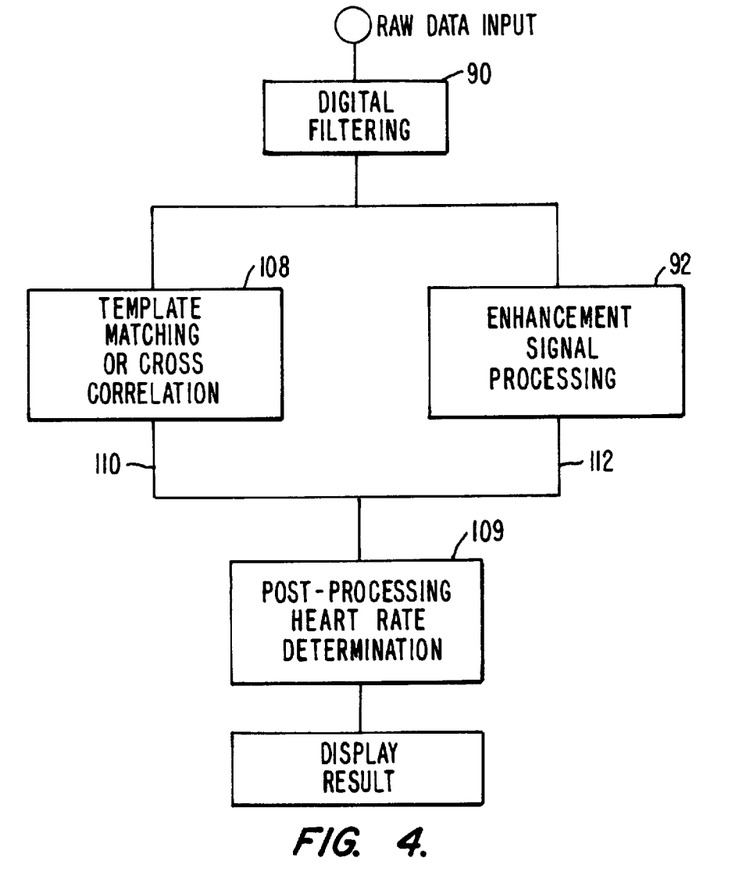
FIG. 4 is an overview flow chart of the software architecture according to the teachings of the invention.

Referring to FIG. 4, there is shown a flow diagram of the main processing carried out by microcontroller 70 on the digital samples received from the AD converter 68. The digital filtering which results in the signals of FIGS. 3D and 3G is represented by the digital filtering block 90. The function of this block is to remove high and low frequency noise from the digital samples.

The digital filtering steps represented by block 90 comprises, in the preferred embodiment, a first step of low pass filtering the incoming digital data with a low pass filter having a notch at 60 Hertz and then passing the resulting filtered data through a bandpass filter which amplifies the signals in a frequency range from 10–40 Hertz and has a notch at 60 Hertz. The reason a low pass filtering step is used prior to passing the data through is to remove remaining undesired high frequency components in the incoming data prior to passing the signals through the bandpass filter for amplification and further filtering.

Figure 5:
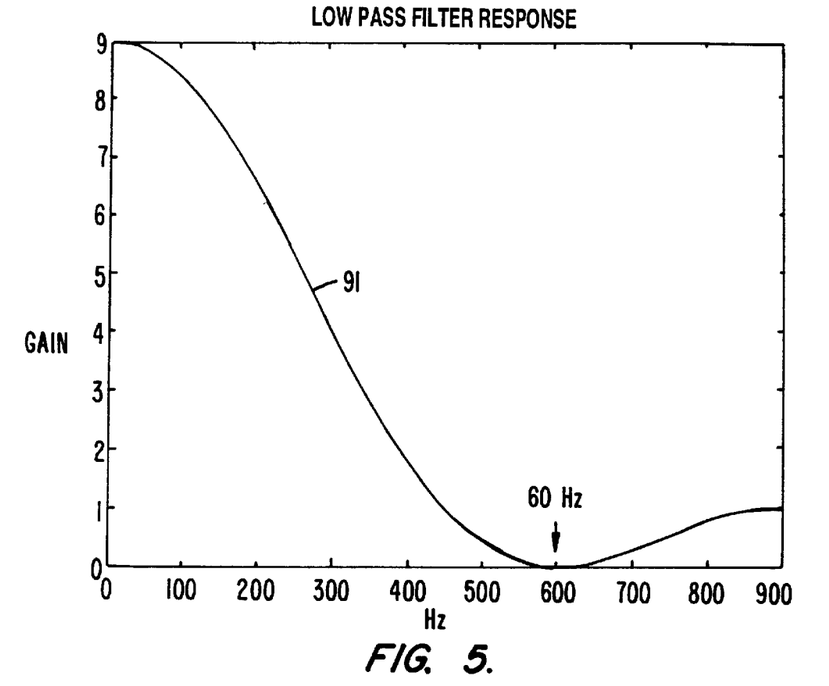
FIG. 5 is a graph of the filter response of a digital low pass filter used in the preferred embodiment of the invention.

FIG. 5 represents the frequency response of the preferred embodiment for the digital low pass filter implemented by the preferred embodiment of the digital filtering step 90 in FIG. 4. This digital filtering is achieved by implementing a recursive filter having integer coefficients to simplify and speed up the calculations required to implement the filter.

However, any digital or analog filter that implements a frequency response roughly equivalent to the frequency response of FIG. 5 will suffice for purposes of practicing the invention, e.g., non-recursive, recursive with different integer coefficients or floating point coefficients, separate DSP etc., analog or any combination of the above. In fact, the low pass filtering step can be eliminated altogether in some embodiments. The purpose of the low pass digital filter is to remove 60 Hertz noise and to enhance signal to noise ratio.

Figure 6:
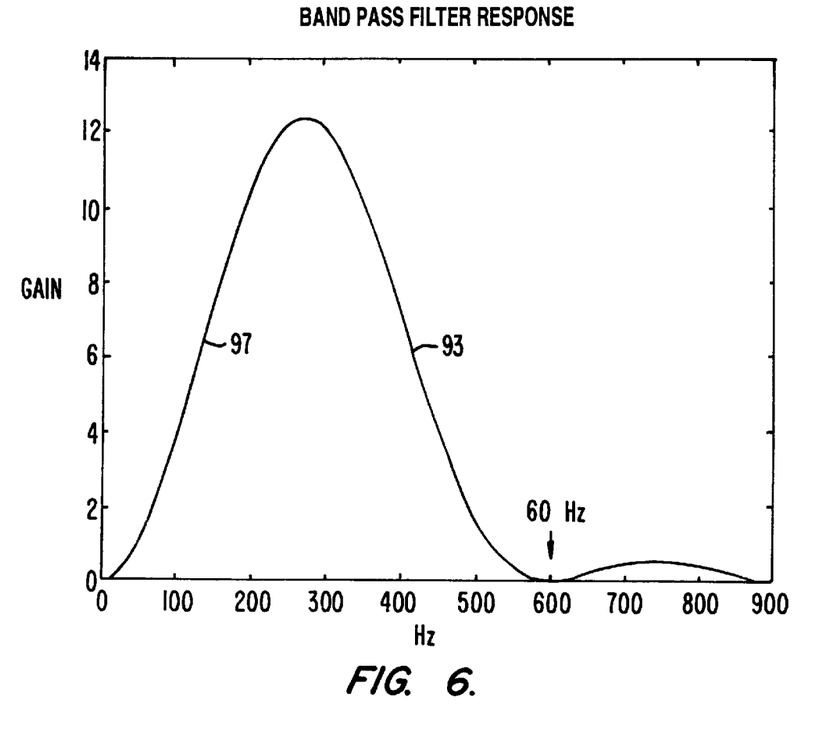
FIG. 6 is a graph of the filter response of a digital bandpass filter used in the preferred embodiment of the invention.
Figure 7:
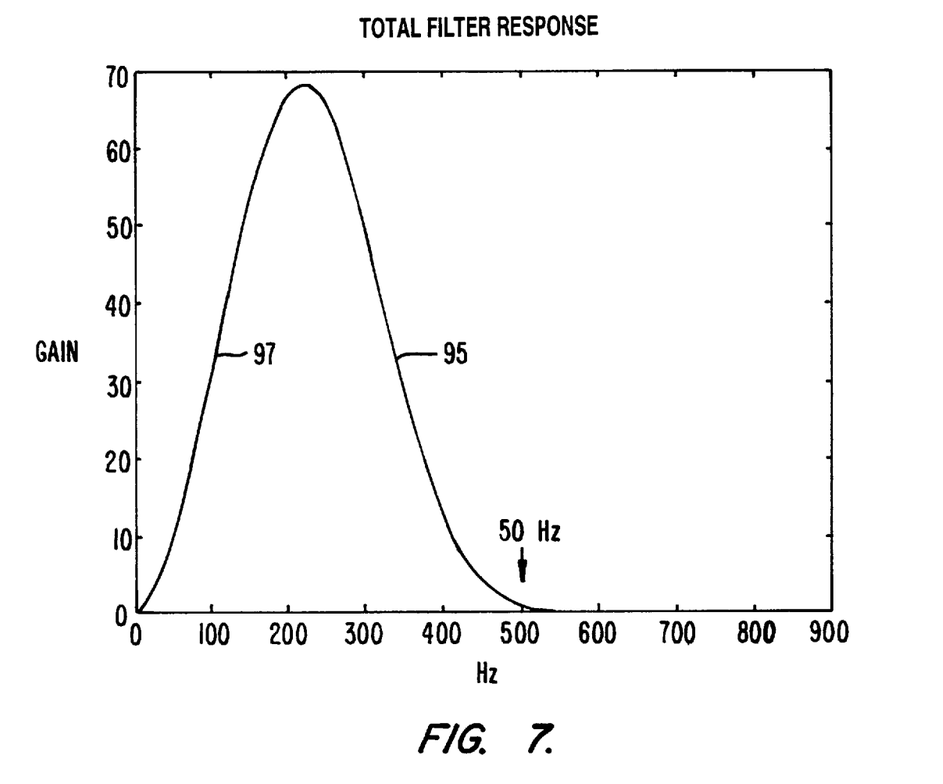
FIG. 7 is a graph of the total filter response resulting from combining the effects of the digital low pass filter and the digital bandpass filter.

FIG. 6 represents the frequency response of the preferred embodiment of the bandpass filter implemented as the second stage of digital filtering represented by block 90 in the preferred embodiment. This digital filtering frequency response is achieved by implementing a recursive filter having integer coefficients to simplify and speed up the calculations required to implement the filter. However, any digital filter that implements a frequency response roughly equivalent to the frequency response of FIG. 6 will suffice for purposes of practicing the invention, e.g., non-recursive, recursive with different integer coefficients or floating point coefficients, separate DSP etc. or any combination of the above. The bandpass filter function could also be done using an analog filter. One purpose of the bandpass filter is to reduce low and high frequency EMG signals caused by exercise, respiration and muscle tremor in addition to further reducing 60 Hertz hum noise. Some of the above mentioned EMG signals lie outside the passband and are therefore attenuated. EMG and other noise signals in the passband are removed by a learning, adaptive threshold detect operation and further uses rules of reason implemented in the software to arbitrate whether pulses which exceed the adaptive threshold are true heart beats or are artifacts or noise.

The low pass filtering step can be eliminated in some alternative embodiments since the bandpass filter also removes the high frequencies. However, the low pass filter is preferred because if it is not present, there is less effective filtering out of 50 Hertz noise which is only an issue if the invention is to be used in any European or other country where 50 Hertz power is used.

Returning to the consideration of the overall digital signal processing represented by FIG. 4, after digital filtering is performed, two different processes are performed to find the EKG signal in the filtered data. In the preferred embodiment, only the enhancement signal processing represented by block 92 is performed. In another embodiment, template matching or cross-correlation is also used to provide alternative results which can be cross-checked against the results of the enhancement signal processing.

Figure 8:
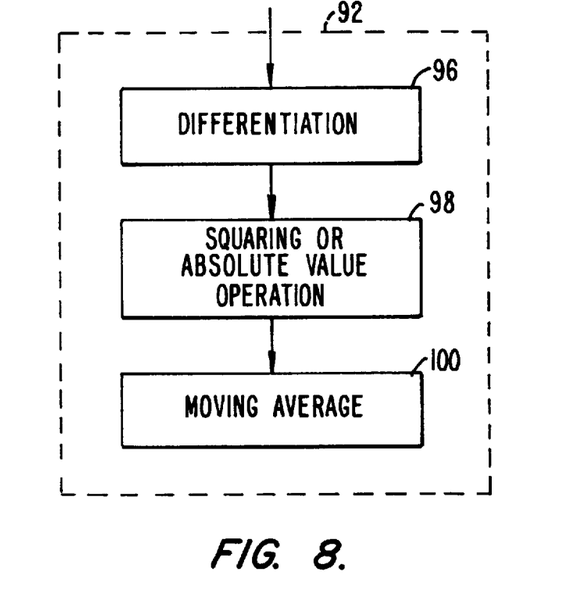
FIG. 8 is a more detailed flow diagram of the enhancement signal processing of the right branch in FIG. 4.
Figure 9A:
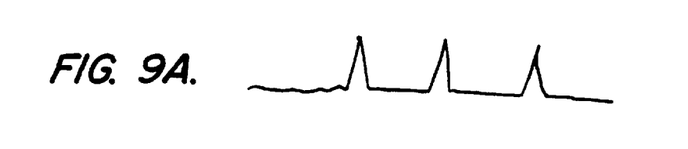
FIGS. 9A–9D are illustrations of the waveforms that illustrate the operation of the processing of FIG. 8.

Referring to FIG. 8, there is shown a flow chart of the basic operations that are performed in the enhancement signal processing block 92. The first step is differentiation, represented by block 96. The reason this differentiation operation is performed is because the filtering process removed some of the information content of the EKG signal, but there is still a fairly high spectral content of high frequency Fourier components of the EKG signal caused by the Q, R and S peaks which is within the passband of both the analog and the digital filters. To enhance this component, the differentiation process is performed on the array of sample data to find the slopes of all peaks in the data. The incoming filtered data has a signal waveform which can look like the waveform in FIG. 9A. The differentiation process receives this waveform and outputs a waveform that looks like the signal in FIG. 9B.

Figures 9B, 9C:
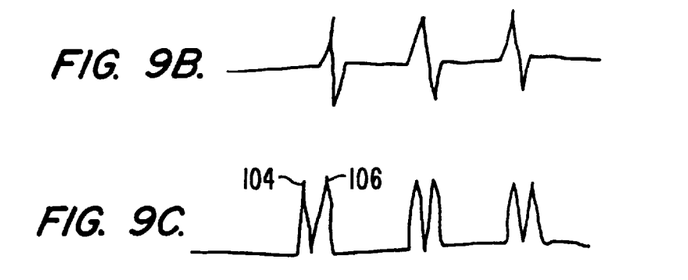

The slopes of the two sides of each peak in the signal FIG. 9C are successively positive and then negative. Because a moving average (an integration step) is to be calculated to smooth out the output of the enhancement signal processing output and to improve the signal to noise ratio, negative peaks are undesirable because they tend to cancel positive peaks and make the signal to noise ratio worse. To get rid of the negative peaks and possibly improve the signal to noise ratio, in the preferred embodiment, a squaring operation represented by block 98 is performed. The squaring operation outputs a waveform like that shown on time line C of FIG. 9. Note that all negative peaks are converted to positive peaks.

Because squaring requires multiplication, and because multiplication is slow and consumes too much computing resource, the preferred embodiment is to substitute a look up table containing the squares of all values likely to be found in the input signal to avoid the processing necessary in multiplication. This is much faster than actually performing the multiplication. In an alternative embodiment, an "absolute value" step can be performed for block 98. This absolute value operation receives both positive and negative peaks and outputs a signal which is all positive peaks, each representing the absolute value of the magnitude of a corresponding positive or negative peak. Squaring is preferred since this has the effect of multiplying the size of the peaks in the signal thereby enhancing the signal to noise ratio. More than one squaring operation may be applied, preferably two, to further enhance the signal-to-noise ratio.

Finally, a moving average is computed as represented by block 100. The purpose of calculating this moving average is to smooth out any sharp spike-like peaks in the output of the squaring operation or absolute value step. The moving average computation is like an integration which calculates the area under each peak in the output from the squaring or absolute value step. The moving average step also increases the signal to noise ratio by taking each pair of peaks in the signal output by block 98 and summing the area under each curve. This enhances the amplitude of the resulting single peak which results from each pair of adjacent peaks in the signal in FIG. 9C. For example, peak 102 results in the output of the moving average step from the integration or filtering of the pair of peaks 104 and 106 that arrived from the squaring step. The moving average is calculated by taking a predetermined number of sequential samples and adding their values and then dividing the sum by the number of samples so added. The individual samples in each moving average can be weighted in some embodiments. This process is carried out continuously for each contiguous group of samples.

Equation (1) below represents the mathematical expression which completely specifies the digital signal processing which implements the recursive low pass filter step of block 90 in FIG. 4 with a notch at 60 Hertz.

Equation (1):

$$Y_n = 1/8 * (2Y_{n-1} + Y_{n-2} + X_n - 2X_{n-3} + X_{n-6})$$

The Y terms represent previous outputs such that $Y_{n-1}$ represents the most recent previous output while $Y_{n-2}$ represents the second most recent previous output. The X terms represent recent data, except that the result of a previous stage's calculation, e.g., $Y_n$ in equation 1 becomes raw data point $X_n$ for the next stage, e.g., $X_n$ in Equation (2) below is actually the result $Y_n$ from the calculation process represented by Equation (1). For example $X_n$ represents the most recent data while $X_{n-4}$ represent the fourth most recent data and so on. Note how the coefficients of the recursive filter specification represented by Equation (1) are all integers thereby greatly speeding up and simplifying the calculation. There are many different combination of coefficients which can result in acceptable filter transfer functions. There may even be other filter specifications with more points or different subscripts which result in acceptable filter responses. Equation (1) only represents one acceptable example, and any alternative that results in a similar range of frequencies in the passband as shown in FIG. 5, and relatively similar gain levels will be acceptable. The factor 1/8 in the equation of Equation (1) is a normalization factor based upon the gain of the filter.

Equation (2) represents the mathematical expression which completely specifies the digital signal processing which implements the recursive bandpass filter step of block 90 in FIG. 4 with a notch at 60 Hertz.

Equation (2):

$$Y_n = 1/12(2Y_{n-1} - 3Y_{n-2} + 2Y_{n-3} - Y_{n-4} + X_n - 2X_{n-6} + X_{n-12})$$

The same can be the about other possible alternatives to the filter specification of Equation (2) as was said about Equation (1). The factor 1/12 in the equation of Equation (2) is a normalization factor based upon the gain of the filter.

Equation (3) represents the mathematical expression which completely specifies the digital signal processing which implements the differentiation step 96 in FIG. 8.

Equation (3):

$$Y_n = 1/4 * (2*X_n + X_{n-1} - X_{n-3} - 2*X_{n-4})$$

Many other combinations of weighting coefficients, numbers of sample points and possibly even different subscripts exist. For example, the denominator 4 in Equation (3) is chosen so as to make the result of the differentiation process larger such that the input data to the squaring process is larger. This results in greater dynamic range. However, other denominator factors exist which can be used without departing from the invention defined in the claims. Any such combination that result in a filter characteristic that has the same relative range of frequencies within the first major loop of the transfer function where most of the useful work gets done will be acceptable to practice the invention. For example, different numbers of sample points with a different divisor will also work to practice the invention.

Equation (4) represents the mathematical expression which completely specifies the digital signal processing which implements the moving average step 100 in FIG. 8.

Equation (4):

$$\frac{1}{8} \sum_{i=0}^{7} X_{N-i} \quad \text{Equation (4):}$$

The moving average function has the effect of amplifying the low frequency components. The number of points selected for the "window" over which the moving average is calculated is important in that it defines where the first notch is in the transfer function which has the characteristic of defining how high the amplitude is of the resulting moving average peak. Eight points were selected in the preferred embodiment to enhance the signal-to-noise ratio by raising the amplitude of the peak that results from each peak pair in the signal from the squaring or absolute value operation of block 98 in FIG. 8. Other values for signal-to-noise ratio would also work, but perhaps not as well. For example, 16 points would smooth the output more, but the amplitude of the peak is lower. A number of points fewer than 8 may result in a sharper peak with more adjacent noise thereby resulting in lower signal to noise ratio. The 1/64 factor in front of the summation is a scaling factor which can be used as a digital gain control factor. In some embodiments, the adaptive learning process will be used to affect this digital gain control factor based upon characteristics found in the sample data.

Referring again to FIG. 4, in an alternative embodiment, a second type of signal processing of the digital data after digital filtering is carried out as a cross check against the results of the enhancement signal processing or as an alternative thereto. The alternative or additional processing is symbolized by block 108 and involves template matching in the preferred embodiment or cross-correlation where adequate processing power is available to do the multiplications involved in the cross-correlation calculation. The template matched filtering is basically a crude but fast way of performing rudimentary cross-correlation to determine the degree of likeness between two waveforms. Template matching is discussed in greater detail in the parent application, U.S. Pat. application No. 08/554,373.

Figure 9D:
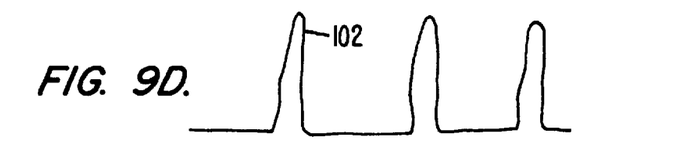

The processes of block 108 and 92 in FIG. 4 have the effect of removing artifacts and noise and enhancing the peaks in the incoming data which are likely to be actual QRS EKG waveforms. In the process of block 92, the differentiation step of block 96 in FIG. 8 tends to remove or suppress EMG peaks and enhance EKG peaks because the EKG peaks have steeper slopes and sharper tips than typical EMG waveforms. This results in larger numbers being output from the differentiator for EKG signals that have been differentiated than for EMG signals. This fact translates to higher peaks in both the positive and negative amplitudes in the signals on time line B of FIG. 9 representing the differentiator results from differentiating EKG QRS waveforms than result from differentiation of typical EMG pulses. This further suppresses EMG noise and enhances the signal to noise ratio.

The template matching or cross-correlation process of block 108 removes artifacts by virtue of suppressing peaks that do not have the shape of the template. The template is designed to simulate closely the shape of the QRS waveform in a typical EKG waveform. In some embodiments, the shape of the template will be adjusted "on-the-fly" after actual EKG signals are isolated for this particular user so as to more closely match the shape of the QRS waveform of this particular user. Suppressing of EMG waveforms and other noise and artifacts occurs because these spurious signals do not have the same shape as the template and therefore result in lower correlation peaks in the output data of the template matching process.

After enhancement of the digital data and removal of as many artifacts as possible in the enhancement process, either by the process of block 92 or block 108 in FIG. 4, the resulting digital data is analyzed to determine the user's current heart rate.

This is done by post-processing heart rate determination module 109 in FIG. 4. The process represented by block 109 could be any one of a large number of different types of discrimination or arbitration routines to decide which of the pulses in the filtered, enhanced data from either path 110 or path 112 in FIG. 4 represent actual heart beats and to calculate the heart rate therefrom.

Figure 10:
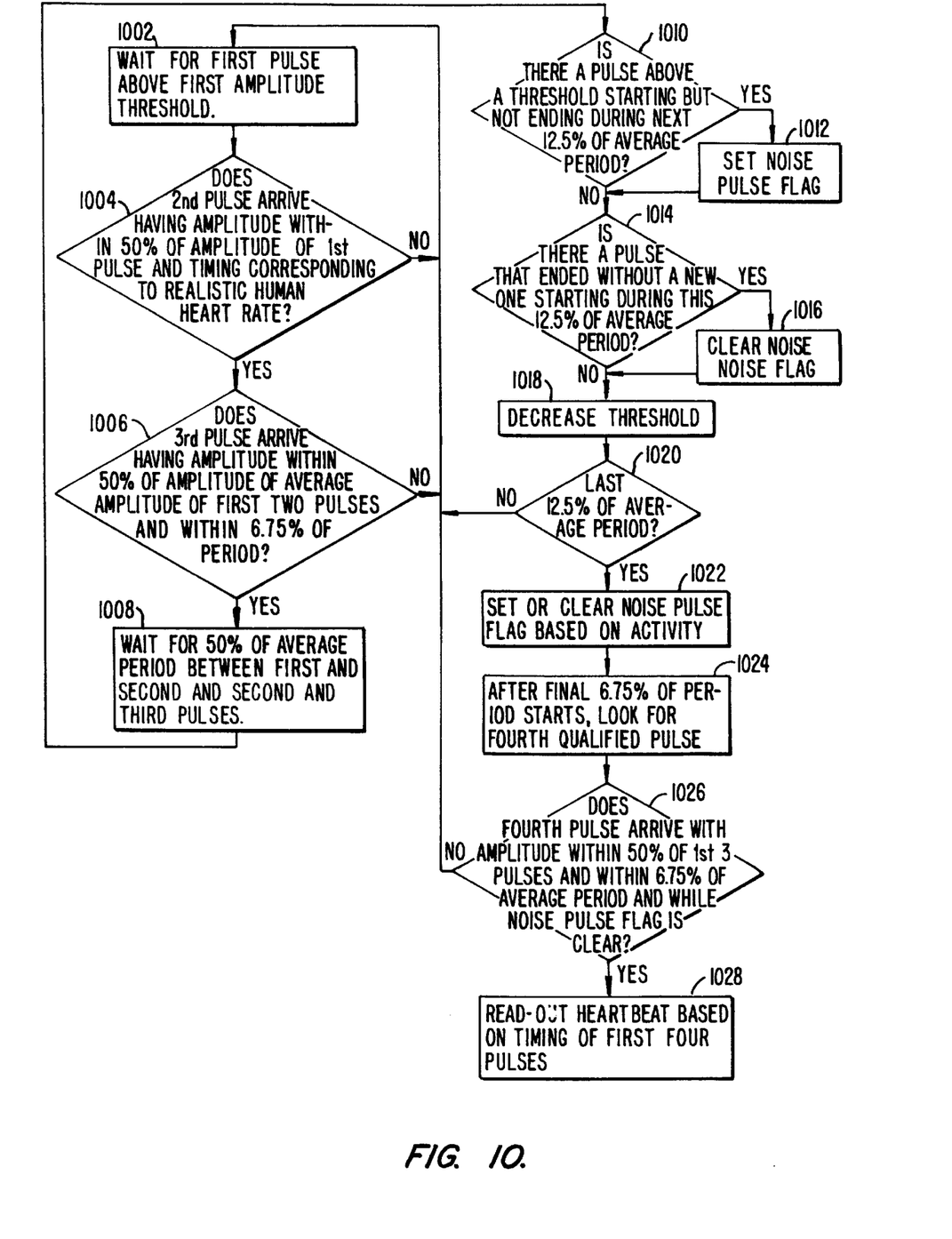
FIG. 10 is a flowchart describing steps of post-processing to determine the user's heart rate.

FIG. 10 is a flowchart describing steps of post-processing to determine the user's heart rate in accordance with one embodiment of the present invention. FIG. 10 shows steps of first establishing that a series of pulses correspond to the user's heartbeat. The steps of FIG. 10 rely on both the amplitudes and positions of pulses to establish that a series of pulses correspond to heartbeats rather than noise artifacts that have survived the previous processing stages. At step 1002, post-processing heart rate determination module 109 awaits the first pulse above a predetermined amplitude threshold. In one embodiment, this threshold is ¼ of the full scale value of the A/D converter output. Once this pulse arrives, post-processing heart rate determination module 109, at step 1004, looks for a second pulse having an amplitude within 50% of the amplitude of the first pulse and arriving at a time indicative of a realistic human heart rate, e.g., between 40 and 240 bpm.

If no second pulse meeting these criteria arrives, processing returns to step 1002 to reawait a first pulse. It should be noted that if a second pulse arrives but does not meet the criteria for a second pulse, it may meet the criteria for a first pulse and step 1002 will be skipped. If a second pulse meeting these criteria arrives, this suggests that both the first and second pulse may both be heartbeats. At step 1006, post-processing heart rate determination module 109 awaits a third pulse having 50% of the amplitude of the average amplitude of the first and second pulses and arriving at a time defining an interpulse period having a duration within 6.75% of the interval between the first pulse and the second pulse.

If no such third pulse arrives, the first two pulses are discarded and processing returns to step 1002 to await a new first pulse. If a third pulse meeting the criteria arrives, post-processing heart rate determination module 109 begins a process of confirming the current measured heart rate by awaiting a fourth pulse. However, post-processing heart rate determination module 109 takes extra precautions to insure that the fourth pulse is not noise. First, at step 1008, post-processing heart rate determination module 109 waits for 50% of an average period determined to be the average of the period between the first and the second pulses and the period between the second and the third pulses.

Post-processing heart rate determination module 109 then looks for a noise pulse that might begin before the expected arrival of the fourth pulse and extend into the expected arrival period. In one embodiment, the threshold for detecting such noise pulses starts at approximately 50% of the mean amplitude of the first three pulses and decreases in four steps to approximately 19% of the mean amplitude. At step 1010, post-processing heart rate determination module 109 spends the next 12.5% (or fourth of the remaining time) of the period until the expected arrival of the fourth pulse checking for a noise pulse having an amplitude above the initial noise pulse threshold of 50%. If such a pulse begins but does not end during this subperiod, then at step 1012, postprocessing heart rate determination module 109 sets a noise pulse flag. If no such pulse arrives, or after step 1012, post-processing heart rate determination module 109 checks if a previous noise pulse ends during this subperiod without a new one starting, at step 1014. If a previous pulse ends, then the noise pulse flag clears at step 1016. After the noise pulse flag clears, or if the noise pulse flag is not cleared, at step 1018, the noise pulse threshold is lowered for the next subperiod of the last 50% of the period before the expected arrival of the fourth pulse. Then post-processing heart rate determination module 109 checks at step 1020 whether, the next 12.5% subperiod is the last before the expected arrival of the fourth pulse. If the next subperiod is not be the last, postprocessing heart rate determination module 109 returns to step 1010 to adjust the noise pulse flag.

If the next 12.5% subperiod is the last, at step 1022, the preferred embodiment sets and clears the noise pulse flag based on any detected pulse activity. The noise pulse threshold has now stepped down to its minimum. Once the last 6.75% of the expected interpulse period arrives, a new pulse may be the expected heartbeat. If, at step 1026, a pulse arrives within 6.75% of the expected arrival time, and having amplitude within 50% of the average of the first three qualified pulses, and while the noise pulse flag is clear, then this is considered to be the fourth qualified pulse and the heart rate based on the first four qualified pulses is read out at step 1028. Requiring the noise pulse flag to be clear eliminates artifacts caused by earlier noise pulses extending into the expected arrival time of the fourth pulse. If no such fourth pulse arrives, the first three pulses are discarded and post-processing heart rate determination module 109 proceeds to step 1002 to await a new first pulse.

Figure 11:
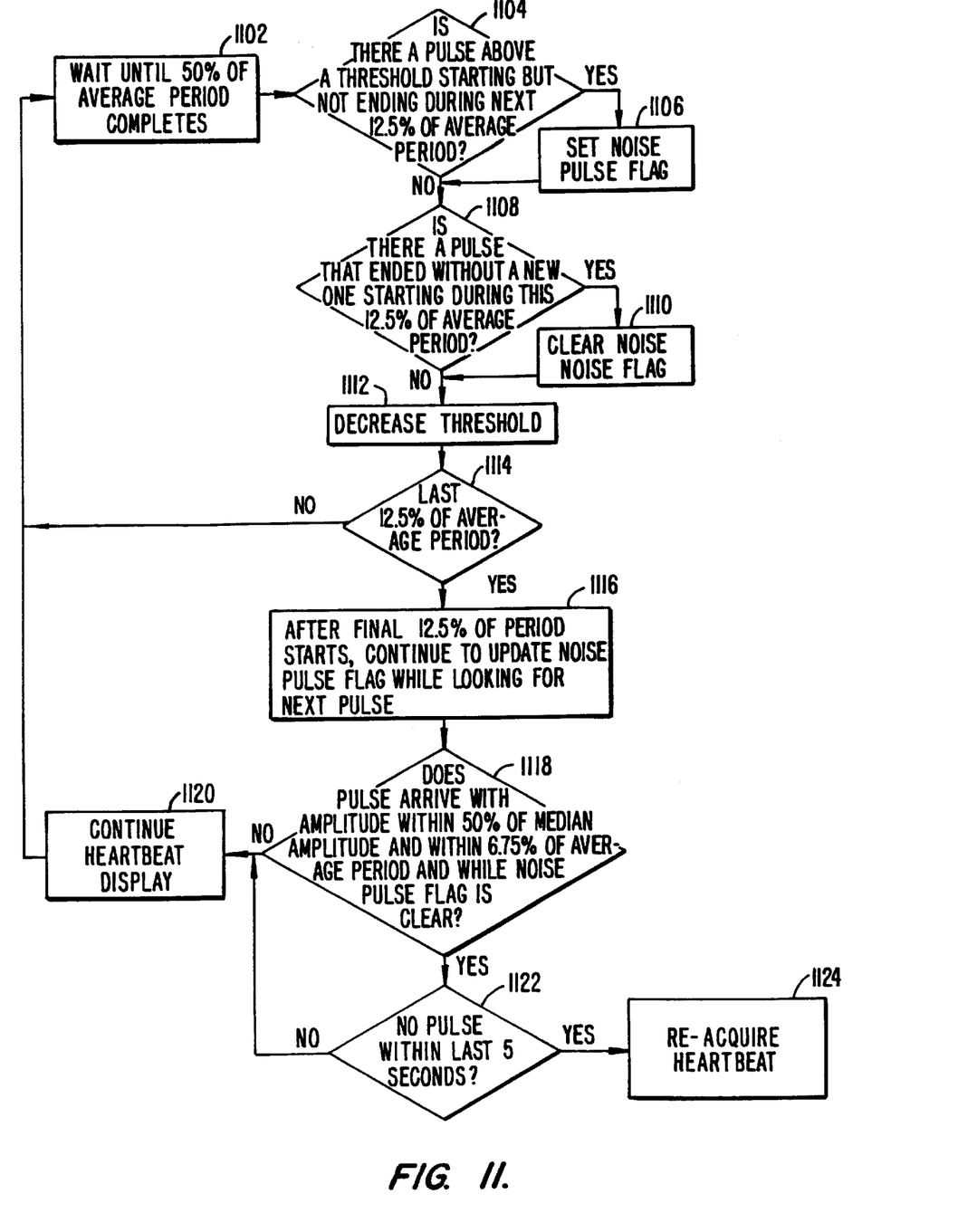
FIG. 11 is a flowchart describing further steps of post-processing to determine the user's heart rate.

After step 1028, post-processing heart rate determination module 109 may be considered to be in a steady state, with a current displayed heart rate being based on the current average period between pulses. However, post-processing heart rate determination module 109 continues to guard against erroneous readings caused by noise. The process of qualifying successive pulses as heartbeats is similar to the steps of qualifying the fourth pulse as shown in FIG. 10. In facts, steps 1102, 1104, 1106, 1108, 1110, 1112, and 1114 are essentially identical to steps 1002–1020 of FIG. 10. In FIG. 11, post-processing heart rate determination module 109 looks for noise pulses during the last 50% of the period between the last heartbeat and the expected arrival time of the next heartbeat as determined by the mean interpulse period. At step 1116, during the last 12.5% of this interpulse period, post-processing heart rate determination module 109 continues to set and clear the noise pulse flag based on received noise pulses but also awaits the next heartbeat pulse during the last 6.75% of the interpulse period. At step 1118, post-processing heart rate determination module 109 determines if a pulse arrives within 50% of the median amplitude, within 6.75% of the average period, and while the noise pulse flag is clear. If such a pulse arrives, heartbeat display continues at step 1120.

If no such pulse arrives, then post-processing heart rate determination module 109 checks at step 1122 whether a qualified pulse has in fact arrived in the last five seconds. If no qualified pulse has arrived in the last five seconds, it is necessary to reacquire the heartbeat at step 1124 by repeating the steps of FIG. 10. If a qualified pulse has arrived in the last five seconds, heartbeat display continues at step 1120 and post-processing heart rate determination module 109 repeats the steps of FIG. 11, looking for a new qualified pulse at the next expected arrival time.

In the foregoing specification, the invention has been described with reference to specific exemplary embodiments thereof. It will, however, be evident that various modifications and changes may be made thereunto without departing from the broader spirit and scope of the invention as set forth in the appended claims and their full scope of equivalents.

What is claimed is:

1. Apparatus for determining heart rate from electrical signals generated within a body, comprising:

at least two electrical contacts for detecting said electrical signals when placed in contact with said body;

an analog circuit that conditions said electrical signals;

an analog-to-digital converter coupled to receive an analog output signal from said analog circuit and convert said analog signals to a plurality of digital samples;

a digital filter for receiving said digital samples and suppressing noise signals that have frequencies below about 5–15 Hertz, and signals having frequencies above about 25–40 Hertz to generate filtered data, said digital filter being a recursive filter having integer coefficients;

an enhancement signal processor to receive said filtered data and highlight signals therein that have predetermined characteristics of QRS complexes in human heartbeat signals so as to generate enhanced digital data, said enhancement signal processor comprising a squaring processor that applies a squaring operation at least twice; and a post-processing heart rate determination signal processor that analyzes said enhanced digital data and determining the heart rate therefrom.

2. The apparatus of claim 1 wherein said analog-to-digital converter uses a sample rate that is a multiple of the powerline AC voltage frequency.

3. The apparatus of claim 1 wherein said enhancement signal processor comprises:

a differentiator for determining the slope of peaks in said filtered data and generating a slope signal which defines the magnitude and sign of the slopes of each portion of each said peak;

said squaring processor for squaring the results from said differentiator at least twice and developing a positive values only signal; and a moving average processor for computing a moving average of said positive values only signal and outputting a moving average signal which defines said moving average over time.

4. The apparatus of claim 3 wherein said differentiator is a digital signal processor which computes the mathematical expression $$Y_n = (2X_n + X_{n-1} - X_{n-3} - 2X_{n-4})/4,$$

where $Y_n$=represents slope at any particular sample time N, $2X_n$=represents twice the amplitude of the most recent digital data sample from the output of the previous filter, $X_{n-1}$=represents the amplitude of the next most recent digital data sample from the output of the previous filter, $X_{n-3}$=represents the amplitude of the third most recent digital data sample in the stream from the output of the previous filter, and $2X_{n-4}$=represents twice the amplitude of the fourth most recent digital data sample from the output of the previous filter.

5. The apparatus of claim 3 wherein said moving average processor comprises means for calculating said moving average as a stream of digital data samples with the most recent digital data sample representing the moving average represented by $Y_N$ and for calculating each $Y_N$ in said moving average data stream by summing the 8 most recent data samples in said stream of data samples representing said filtered data and dividing the sum by 64.

6. The apparatus of claim 1 further comprising a display for displaying said heart rate determined by said post-processing heart rate determination signal processor means.

7. Apparatus for determining heart rate from electrical signals generated within a body, comprising:

at least two electrical contacts for detecting said electrical signals when placed in contact with said body;

an analog circuit that conditions said electrical signals;

an analog-to-digital converter coupled to receive an analog output signal from said analog circuit and convert said analog signals to a plurality of digital samples;

a digital filter for receiving said digital samples and suppressing noise signals that have frequencies below about 5–15 Hertz, and signals having frequencies above about 25–40 Hertz to generate filtered data, said digital filter being a recursive filter having integer coefficients;

an enhancement signal processor to receive said filtered data and highlight signals therein that have predetermined characteristics of ORS complexes in human heartbeat signals so as to generate enhanced digital data; and a post-processing heart rate determination signal processor that analyzes said enhanced digital data and determining the heart rate therefrom; and wherein said analog circuit comprises;

a differential amplifier having a gain of from approximately 1–10 coupled to said electrical contact means for amplifying any signals detected by said electrical contact means and suppressing any common mode noise; and an analog bandpass filter coupled to receive the output of said differential amplifier and having a passband from approximately 5 to 40 Hertz, said bandpass filter comprising a low pass analog active filter having a first order rolloff characteristic with a corner frequency between 25 and 40 Hertz, and a high pass analog active filter having a second order rolloff characteristic with a corner frequency between 5 and 15 Hertz.

8. A method of detecting a heartbeat rate among unwanted signals, comprising the steps of:

sensing signals from a body using electrodes in contact, with the skin of the body;

amplifying said signals while cancelling common mode noise therein;

filtering out noise below and above the frequency range in which the desired heartbeat rate will lie;

converting the filtered analog signal to a plurality of digital samples;

digitally filtering the digital samples to remove further remnants of frequencies above and below the range of frequencies in which said heartbeat will lie and to suppress powerline hum at approximately 50–60 Hertz so as to generate filtered digital samples;

digitally processing said filtered digital samples to enhance heartbeat peaks in the signals represented by said filtered digital samples to generate enhanced digital samples;

processing said enhanced digital samples to determine said heartbeat rate.

9. The method of claim 8 wherein the step of digitally filtering the digital samples comprises the step of recursively filtering the sample data derived from the signals sensed from said body according to the following recursive filter specifications, recursively low pass filtering according to the equation:

$$Y_n = \frac{1}{8}(2Y_{n-1} - Y_{n-2} + X_n 2X_{n-3} + X_{n-6})$$

where, $Y_n$ represents the output digital sample on each iteration, $Y_{n-1}$ and $Y_{n-2}$ represent previous outputs such that $Y_{n-1}$ represents the most recent previous output while $Y_{n-2}$ represents the second most recent previous output, and wherein X terms including $X_n$, $X_{n-3}$ and $X_{n-6}$ represent recent raw data inputs such that $X_n$ represents the most recent raw data input, $X_{n-3}$ represents the 3rd most recent raw data input and $X_{n-6}$ represents the 6th most recent raw data input, and recursively bandpass filtering according to the equation:

$$Y_n = \frac{1}{12}(2Y_{n-1} - 3Y_{n-2} + 2Y_{n-3} - Y_{n-4} + X_n - 2X_{n-6} + X_{n-12})$$

where, $Y_n$ represents the output digital sample of the bandpass filtering step on each iteration, and $Y_{n-1}$ and $Y_{n-2}$ represent previous output digital samples of the bandpass filtering step such that $Y_{n-1}$ represents the most recent previous output while $Y_{n-2}$ represents the second most recent previous output, and $Y_{n-3}$ represents the third most previous output, and wherein X terms including $X_n$, $X_{n-6}$ and $X_{n-12}$ represent recent sample inputs including samples derived from the raw or analog filtered data or digital sample results of a previous stage's calculation which includes the digital low pass filtering step, and $X_{n-6}$ represents the 6th most recent data input from the previous stage and $X_{n-12}$ represents the 12th most recent raw data input from the previous stage.

10. The process of claim 9 wherein said process of digitally enhancing comprises the steps of:

using a computer to differentiate the samples output from said recursive bandpass filter to determine the slope of peaks encoded in said digital sample data, and outputting differentiator digital samples encoding the results of said differentiating operation;

using a computer to square the amplitude of signals encoded in said differentiator digital samples by looking up the squares in a lookup table so as to generate squared digital samples; and using a computer to compute the moving average of said squared digital samples.

11. The process of claim 10 wherein said step of using a computer to calculate said moving average comprises the steps of:

using a computer to calculate a moving average of said squared digital samples according to the mathematical expression, $$Y_N = \frac{1}{8} \sum_{i=0}^{7} X_{N-i}$$

where $Y_N$ represents moving average at any particular sample time N, $X_{N-i}$ = represents the amplitude of the digital data sample at time N−i.

12. Apparatus for determining heart rate from electrical signals generated within a body, comprising:

at least two electrical contacts for detecting said electrical signals when placed in contact with said body;

an analog circuit that conditions said electrical signals;

an analog-to-digital converter coupled to receive an analog output signal from said analog circuit and convert said analog signals to a plurality of digital samples;

a digital filter for receiving said digital samples and suppressing unwanted signals;

an enhancement signal processor to receive said filtered data and highlight signals therein that have predetermined characteristics of QRS complexes in human heartbeat signals so as to generate enhanced digital data, said enhancement signal processor comprising:

a differentiator for determining the slope of peaks in said filtered data and generating a slope signal which defines the magnitude and sign of the slopes of each portion of each said peak;

a squaring processor for squaring the results from said differentiator at least twice; and a moving average processor for computing a moving average of said positive values only signal and outputting a moving average signal which defines said moving average over time.

13. In a heart rate monitoring system wherein heart activity is converted to electrical signals, a method for distinguishing pulses caused by heartbeats from other pulses comprising the steps of:

a) discarding pulses that arrive at times inconsistent with plausible beat-to-beat variation in heartbeat rate as representing artifacts rather than heartbeats;

b) discarding pulses having amplitudes varying more than a predetermined amount from previously received pulses representing heartbeats;

c) identifying an artifact pulse arriving before an expected arrival time of a heartbeat pulse; and d) identifying a pulse that arrives at said expected arrival time as a heartbeat pulse only if said artifact pulse has subsided.

14. The method of claim 13 wherein said a) step comprises discarding pulses that arrive at a time indicative of a change of period between heartbeats greater than approximately 6.75%.

15. The method of claim 13 wherein said b) step comprises discarding pulses that have amplitudes varying more than 50% from previously received pulses representing heartbeats.

16. The method of claim 13 wherein said c) step comprises the steps of:

after approximately 50% of a period between a last heartbeat pulse and said expected arrival time of a heartbeat pulse, setting a noise pulse threshold for detecting artifact pulses;

lowering said noise pulse threshold until said expected arrival time; and identifying non-heartbeat pulses above said noise pulses threshold as artifact pulses.

17. In a heart rate monitoring system wherein heart activity is converted to electrical signals, a post-processing heartbeat determining system that distinguishes heartbeat pulses from other pulses said system comprising:

an analog to digital converter that converts said electrical signal to digital samples; and a digital circuit adapted to digitally process said digital samples to determine times of said pulses; discard pulses that arrive at times inconsistent with plausible beat-to-beat variation in heartbeat rate as representing artifacts rather than heartbeats; and discard pulses having amplitudes varying more than a predetermined amount from previously received pulses representing heartbeats.

18. The system of claim 17 wherein said digital circuit is further adapted to identify an artifact pulse arriving before an expected arrival time of a heartbeat pulse; and identify a pulse that arrives at said expected arrival time as a heartbeat pulse only if said artifact pulse has subsided.

19. The system of claim 17 wherein said digital circuit is further adapted to discard pulses that arrive at a time indicative of a change of period between heartbeats greater than approximately 6.75%.

20. The system of claim 17 wherein said digital circuit is further adapted to discard pulses that have amplitudes varying more than 50% from previously received pulses representing heartbeats.

21. The system of claim 18 wherein said digital circuit after approximately 50% of a period between a last heartbeat pulse and said expected arrival time of a heartbeat pulse, is further adapted to:

set a noise pulse threshold for detecting artifact pulses;

lower said noise pulse threshold until said expected arrival time; and identify non-heartbeat pulses above said noise pulse threshold as artifact pulses.

* * * * *